US012169593B2

(12) United States Patent
Curtis

(10) Patent No.: US 12,169,593 B2
(45) Date of Patent: Dec. 17, 2024

(54) SYSTEM AND METHOD FOR DISTRIBUTING REVENUE AMONG USERS BASED ON QUANTIFIED AND QUALIFIED EMOTIONAL DATA

(71) Applicant: Steve Curtis, Vancouver (CA)

(72) Inventor: Steve Curtis, Vancouver (CA)

( * ) Notice: Subject to any disclaimer, the term of this patent is extended or adjusted under 35 U.S.C. 154(b) by 148 days.

(21) Appl. No.: 17/278,528

(22) PCT Filed: Sep. 21, 2019

(86) PCT No.: PCT/IB2019/058004
§ 371 (c)(1),
(2) Date: Mar. 22, 2021

(87) PCT Pub. No.: WO2020/058944
PCT Pub. Date: Mar. 26, 2020

(65) Prior Publication Data
US 2022/0026988 A1    Jan. 27, 2022

Related U.S. Application Data

(60) Provisional application No. 62/734,471, filed on Sep. 21, 2018.

(51) Int. Cl.
*G06F 3/01*    (2006.01)
*A61B 5/00*    (2006.01)
(Continued)

(52) U.S. Cl.
CPC .............. *G06F 3/015* (2013.01); *A61B 5/165* (2013.01); *A61B 5/6802* (2013.01);
(Continued)

(58) Field of Classification Search
CPC ....... G06F 3/015; A61B 5/165; A61B 5/6802; G06Q 30/0601; G06Q 30/0214; G16H 40/60
(Continued)

(56) References Cited

U.S. PATENT DOCUMENTS 8,788,495 B2    7/2014    Shu
9,653,097 B2    5/2017    Hirose
(Continued)

FOREIGN PATENT DOCUMENTS

CN    105391843 A    3/2016
CN    105726045 A    7/2016
(Continued)

OTHER PUBLICATIONS

International Search Report and Written Opinion from PCT Application No. PCT/IB2019/058004, dated Jan. 27, 2020.
(Continued)

*Primary Examiner* — Tom V Sheng
(74) *Attorney, Agent, or Firm* — Jacob M. Ward; Ward Law Office LLC

(57) ABSTRACT

A system and method for distributing revenue among users based on quantified emotional data and qualified emotional data of the corresponding users. The method includes the step of collecting biorhythm data of the user through a wearable user device. The method includes the step of receiving the biorhythm data through a computing unit. The method includes the step of analyzing the received biorhythm data and computing an emotional score of each user through an algorithmic module. The method includes the step of monitoring the emotional score of each user through a tracking module. The method includes the step of sending a referral to potential users to perform actions pertaining to a platform and product through a referral module. The method includes the step of computing individual total sub score for each user using the quantified emotional data and the qualified emotional data for an interval of time through a first computation module. The method includes the step of computing one or more subtotal scores based on calculations performed on the referrals of each user and a plurality of
(Continued)

related referrals corresponding to each user through an nth computation module. The nth computation module computes the subtotal scores for each user based on data of the individual user on the platform. The method includes the step of combining the individual subtotal score computed by the first computation module and subtotal score computed by the nth computation module to obtain a single score for each user through a final computation module. The method includes the step of generating revenue when the potential users perform actions pertaining to the platform and the product and distribute a predefined amount of money to each user based on a plurality of parameters through a revenue distribution module.

5 Claims, 3 Drawing Sheets

(51) Int. Cl.
*A61B 5/16* (2006.01)
*G06Q 30/0601* (2023.01)
*G06Q 30/0214* (2023.01)
*G16H 40/60* (2018.01)

(52) U.S. Cl.
CPC ..... *G06Q 30/0601* (2013.01); *G06Q 30/0214* (2013.01); *G16H 40/60* (2018.01)

(58) Field of Classification Search
USPC ......................................................... 345/156
See application file for complete search history.

(56) References Cited

U.S. PATENT DOCUMENTS

| | | | |
|---|---|---|---|
| 9,983,670 B2 | 5/2018 | Coleman et al. | |
| 10,120,413 B2 | 11/2018 | Aimone et al. | |
| 10,289,076 B2* | 5/2019 | Kim ....................... | G06N 3/008 |
| 10,600,507 B2 | 3/2020 | Bostick et al. | |
| 10,881,348 B2 | 1/2021 | Levine et al. | |
| 2009/0177607 A1* | 7/2009 | Matsushima ........... | G06F 16/40 |
| | | | 707/E17.014 |
| 2009/0222302 A1 | 9/2009 | Higgins et al. | |
| 2010/0250554 A1 | 9/2010 | Shu | |
| 2012/0259240 A1 | 10/2012 | Llewellyn et al. | |
| 2013/0198694 A1 | 8/2013 | Rahman et al. | |
| 2014/0073486 A1 | 3/2014 | Ahmed et al. | |
| 2014/0089399 A1 | 3/2014 | Chun et al. | |
| 2014/0221866 A1 | 8/2014 | Quy | |
| 2014/0223462 A1 | 8/2014 | Aimone et al. | |
| 2014/0347265 A1 | 11/2014 | Aimone et al. | |
| 2016/0042749 A1 | 2/2016 | Hirose | |
| 2016/0077547 A1 | 3/2016 | Aimone et al. | |
| 2017/0083506 A1* | 3/2017 | Liu ....................... | G06V 40/174 |
| 2017/0143246 A1 | 5/2017 | Flickinger | |
| 2017/0300655 A1* | 10/2017 | Lane ....................... | G16H 10/60 |
| 2017/0315699 A1 | 11/2017 | Markus et al. | |
| 2017/0319074 A1 | 11/2017 | Lim | |
| 2017/0337476 A1 | 11/2017 | Gordon et al. | |
| 2018/0032126 A1 | 2/2018 | Liu | |
| 2018/0032682 A1 | 2/2018 | Donalds | |
| 2018/0035938 A1 | 2/2018 | El Kaliouby et al. | |
| 2018/0101776 A1 | 4/2018 | Osotio et al. | |
| 2018/0206725 A1* | 7/2018 | Everett ................. | A61B 5/1116 |
| 2018/0232567 A1* | 8/2018 | Dolsma ................... | G09B 7/04 |
| 2018/0303397 A1 | 10/2018 | Krupat et al. | |
| 2019/0159677 A1* | 5/2019 | Soyao .................... | G16H 20/10 |
| 2019/0174190 A1 | 6/2019 | Newell et al. | |
| 2020/0058209 A1 | 2/2020 | Sreedhara | |
| 2021/0005224 A1 | 1/2021 | Rothschild et al. | |
| 2021/0097240 A1* | 4/2021 | Singh .................... | G06F 40/253 |
| 2021/0150150 A1 | 5/2021 | Wu | |
| 2022/0031239 A1* | 2/2022 | Curtis ................... | G16H 80/00 |
| 2022/0036481 A1* | 2/2022 | Curtis ..................... | A61B 5/16 |

FOREIGN PATENT DOCUMENTS

| | | |
|---|---|---|
| JP | 2016036500 A | 3/2016 |
| JP | 2018138155 A | 9/2018 |
| WO | 2011076243 A1 | 6/2011 |
| WO | 2013056191 A1 | 4/2013 |
| WO | 2014137919 A1 | 9/2014 |
| WO | 2020056519 A1 | 3/2020 |
| WO | 2020058942 A1 | 3/2020 |
| WO | 2020058943 A1 | 3/2020 |
| WO | 2020058944 A1 | 3/2020 |

OTHER PUBLICATIONS

International Search Report from PCT Application No. PCT/CA2019/051340, Dec. 23, 2019.
International Search Report from PCT Application No. PCT/IB2019/058002, Dec. 31, 2019.
International Search Report from PCT Application No. PCT/IB2019/058003, Jan. 10, 2020.
Extended European Search Report for Corresponding European Patent Application No. 19863956.9, May 16, 2022.
Extended European Search Report for Corresponding European Patent Application No. 19862251.6, May 19, 2022.
Extended European Search Report for Corresponding European Patent Application No. 19862988.3, May 20, 2022.
Extended European Search Report for Corresponding European Patent Application No. 19863510.4, Jul. 5, 2022.
Chinese Office Action for Corresponding Chinese Patent Application No. 201980076440.6, Oct. 8, 2022.
Indian Office Action for Corresponding Indian Patent Application No. 202127017812, Dec. 1, 2022.
Indian Office Action for Corresponding Indian Patent Application No. 202127017806, Dec. 13, 2022.
Indian Office Action for Corresponding Indian Patent Application No. 202127017809, Dec. 22, 2022.
Indian Office Action for Corresponding Indian Patent Application No. 202127017894, Feb. 7, 2023.
Japanese Office Action for Corresponding Japanese Patent Application No. 2021-540344, May 16, 2023.

* cited by examiner

SYSTEM AND METHOD FOR DISTRIBUTING REVENUE AMONG USERS BASED ON QUANTIFIED AND QUALIFIED EMOTIONAL DATA

TECHNICAL FIELD

The present invention relates to an integrated revenue sharing platform, in particular to a system and method for distributing revenue among users based on quantified emotional data and/or qualified emotional data of the corresponding users.

BACKGROUND ART

Traditionally, word of mouth marketing/advertising of a business is based on the referrals given by the existing users to new users. Further, organizations use business models to financially reward the users on successfully referring the other users to use the business's products/services. These business models are beneficial for the organizations and the users that participate in the referral programs. However, most of the revenue sharing methods are based on the referring total product volume or sales numbers. Further, the existing revenue sharing methods prioritize and incentivize absolute product sales before the actual needs of customers. Additionally, the existing revenue sharing systems and methods do not consider the emotional state of a user to provide any incentive or revenue. Also, the existing systems and method financially reward users that can create negative cooperation between the users. Most of the existing systems and methods in the medical domain do not utilize digital referral programs to financial reward the users for referrals.

U.S. Pat. No. 10,120,413 B2 filed by Aimone et al. discloses a training apparatus with an input device and a wearable computing device with a bio-signal sensor and a display to provide an interactive VR environment for a user. The bio-signal sensor receives bio-signal data from the user. The bio-signal sensor includes a brainwave sensor. VR may provide a computer-simulated experience that replicates, creates or enhances an environment that simulates physical presence in places in the real or non-real world. However, the training apparatus disclosed in Aimone et al. reference does not directly reinforce or incentivize the user to urge others to interact with the training apparatus.

U.S. Pat. No. 9,983,670 B2 filed by Coleman et al. discloses a training method for enabling users to learn how to control their brainwaves so as to enable the use of BCIs. The method decreases the learning curve for using a BCI. The method identifies characteristics of a user's brain state to determine the user's cognitive or emotional state regardless of the user's ability to control a BCI. However, the training method disclosed in Coleman et al. reference is not effective because it does not encourage or reward other potential users to adopt the disclosed training method.

Therefore there is a need for a system and method that strongly incentivize the users to introduce the system to other potential users. As the system has to support the health and wellness of the users, the system needs to be compelling—supported by a strong revenue-distribution financial model. There is a need to reinforce healthy behaviors measured and rewarded based on quantified and qualified emotional data collected on each user. There is also a need for a system and method for distributing revenue among users based on a quantified and qualified emotional data of the corresponding users. Further, there is a need for a system and method for distributing revenue among users based on an optimal experience of the users out of a product or a platform. Furthermore, there is a need for a system and method to incentivize the user based on the emotional improvement of the user, a positive mental state of the user, and an emotional score of the user.

Thus, in view of the above, there is a long-felt need in the industry to address the aforementioned deficiencies and inadequacies.

Further limitations and disadvantages of conventional and traditional approaches will become apparent to one of skill in the art through comparison of described systems with some aspects of the present disclosure, as set forth in the remainder of the present application and with reference to the drawings.

SUMMARY OF INVENTION

A system to distribute revenue among a plurality of users based on at least one of a quantified emotional data and a qualified emotional data of the corresponding users is provided substantially, as shown in and/or described in connection with at least one of the figures, as set forth more completely in the claims.

The present invention provides a method for distributing revenue among a plurality of users based on at least one of a quantified emotional data and a qualified emotional data of the corresponding users. The method includes the step of collecting biorhythm data of the user through a wearable user device configured to be worn on the user's body, near the body, or placed in the user's body (implantable). The method includes the step of receiving the biorhythm data of the users through a computing unit communicatively connected with the wearable user device over a communication network. The method includes the step of analyzing the received biorhythm data and computing an emotional score of each user through an algorithmic module. The method includes the step of monitoring the emotional score of each user through a tracking module. The method includes the step of sending a referral to a plurality of potential users to perform a plurality of actions pertaining to a platform and a product through a referral module. The method includes the step of computing individual total sub score for each user using the quantified emotional data and the qualified emotional data for an interval of time through a first computation module. The method includes the step of computing at least one subtotal score based on calculations performed on the referrals of each user and a plurality of related referrals corresponding to each user and one or more subtotals based on a plurality of other parameters through an nth computation module. The nth computation module computes the subtotal scores for each user based on data of the individual user on the platform. In an aspect, the method identifies all the referred users connected to each user and computes a score for each based on set parameters. For example, this may include a plurality of first-generation referrals, a plurality of second-generation referrals, a plurality of third-generation referrals, and a plurality of nth generation referrals. Once the relevant referred users are identified, different calculations may be used to determine a score for each referred user identified. For instance, third-generation referrals may be multiplied by a smaller weight than first-generation referrals. The nth computation module also computes other types of subtotal scores based on the user's data or actions. The method includes the step of combining the individual subtotal score computed by the first computation module and the one or more subtotal scores computed by the nth computation module to obtain a single score for each user through a final computation module. Various orders of operations may be used to perform this calculation. The method includes the step of generating revenue when the potential users perform the plurality of actions pertaining to the platform and the product through a revenue distribution module. The method includes the step of distributing a predefined amount of money to each user based on a plurality of parameters through the revenue distribution module. The parameters comprising at least one of the computed emotional data scores of the users, and a calculation involving other user's scores present in the user's network on the platform.

In an aspect, the wearable user device includes various sensors to detect one or more parameters pertaining to the emotions of the user.

In an aspect, the referral module facilitates the users to track the status of the sent referrals and one or more received referrals.

In an aspect, the referral module facilitates the users associated with the referrals to establish communication with each other.

In an aspect, the plurality of actions includes access to the platform and purchase of the product.

In an aspect, the potential users perform the actions by clicking on the referral.

Another aspect of the present invention relates to a system to distribute revenue among a plurality of users based on at least one of a quantified emotional data and a qualified emotional data of the corresponding users. The system includes a wearable user device and a computing unit. The wearable user device configured to be worn on the user's body to collect biorhythm data of the user. The computing unit is communicatively connected with the wearable user device to receive the biorhythm data of the users over a communication network. The computing unit includes a processor, and a memory communicatively coupled to the processor. The memory includes an algorithmic module, a tracking module, a referral module, a first computation module, an nth computation module, a final computation module, and a revenue distribution module. The algorithmic module analyzes the received biorhythm data and computes an emotional score of each user. The tracking module monitors the emotional score of each user. The referral module enables the user to send a referral to a plurality of potential users to perform a plurality of actions pertaining to a platform and a product. In an embodiment, the referrals may be sent in various formats such as a hyperlink which can be encoded into an image, a video, a QR code, a sound byte, an ID, a barcode or any other format that is in the hyperlink link form or delivers to a given web address.

The first computation module computes individual total subscore for each user using the quantified emotional data and the qualified emotional data for an interval of time. The nth computation module computes at least one subtotal score based on calculations performed on the referrals of each user and a plurality of related referrals corresponding to each user and one or more subtotals based on a plurality of other parameters. The nth computation module computes the subtotal scores for each user based on data of the individual user on the platform. The final computation module combines the individual subtotal score computed by the first computation module and the subtotal score computed by the nth computation module to obtain a single score for each user. Various orders of operations may be used to perform this calculation. The revenue distribution module generates revenue when the potential users perform the plurality of actions pertaining to the platform and the product. The revenue distribution module distributes a predefined amount of money to each user based on a plurality of parameters. The parameters include but not limited to the computed emotional data scores of the users, and a calculation involving other user's scores present in the user's network on the platform.

Accordingly, one advantage of the present invention is that it provides a transparent revenue sharing platform based on the referrals and emotion-based score.

Accordingly, one advantage of the present invention is that it improves the user's decision-making capabilities, focus on tasks, and productivity.

Accordingly, one advantage of the present invention is that it enables the users to periodically monitor their emotional state to receive increased revenue over a time which theoretically leads to reduced illness and improved mental health.

Accordingly, one advantage of the present invention is that it compels the users to positively interact with the other users and improves the emotional health of the users to elevate their scores and generate additional revenue Accordingly, one advantage of the present invention is that it improves the life of the users and enables organizations as well as the users to earn money along with the proliferation of the product and platform.

Accordingly, one advantage of the present invention is that it incentivizes the users to use and promote the platform.

Accordingly, one advantage of the present invention is that it includes various methods of transmission of the referrals includes but not limited to text message (SMS), social media posts and messages, and embedded links in images and video.

Other features of embodiments of the present invention will be apparent from accompanying drawings and from the detailed description that follows.

Yet other objects and advantages of the present invention will become readily apparent to those skilled in the art following the detailed description, wherein the preferred embodiments of the invention are shown and described, simply by way of illustration of the best mode contemplated herein for carrying out the invention. As we realized, the invention is capable of other and different embodiments, and its several details are capable of modifications in various obvious respects, all without departing from the invention. Accordingly, the drawings and description thereof are to be regarded as illustrative in nature, and not as restrictive.

BRIEF DESCRIPTION OF DRAWINGS

In the figures, similar components and/or features may have the same reference label. Further, various components of the same type may be distinguished by following the reference label with a second label that distinguishes among the similar components. If only the first reference label is used in the specification, the description applies to any one of the similar components having the same first reference label irrespective of the second reference label.

DESCRIPTION OF EMBODIMENTS

The present disclosure is best understood with reference to the detailed figures and description set forth herein. Various embodiments have been discussed with reference to the figures. However, those skilled in the art will readily appreciate that the detailed descriptions provided herein with respect to the figures are merely for explanatory purposes, as the methods and systems may extend beyond the described embodiments. For instance, the teachings presented and the needs of a particular application may yield multiple alternate and suitable approaches to implement the functionality of any detail described herein. Therefore, any approach may extend beyond certain implementation choices in the following embodiments.

References to "one embodiment," "at least one embodiment," "an embodiment," "one example," "an example," "for example," and so on indicate that the embodiment(s) or example(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment.

Methods of the present invention may be implemented by performing or completing manually, automatically, or a combination thereof, selected steps or tasks. The term "method" refers to manners, means, techniques and procedures for accomplishing a given task including, but not limited to, those manners, means, techniques, and procedures either known to, or readily developed from known manners, means, techniques and procedures by practitioners of the art to which the invention belongs. The descriptions, examples, methods, and materials presented in the claims and the specification are not to be construed as limiting but rather as illustrative only. Those skilled in the art will envision many other possible variations within the scope of the technology described herein.

Figure 1:
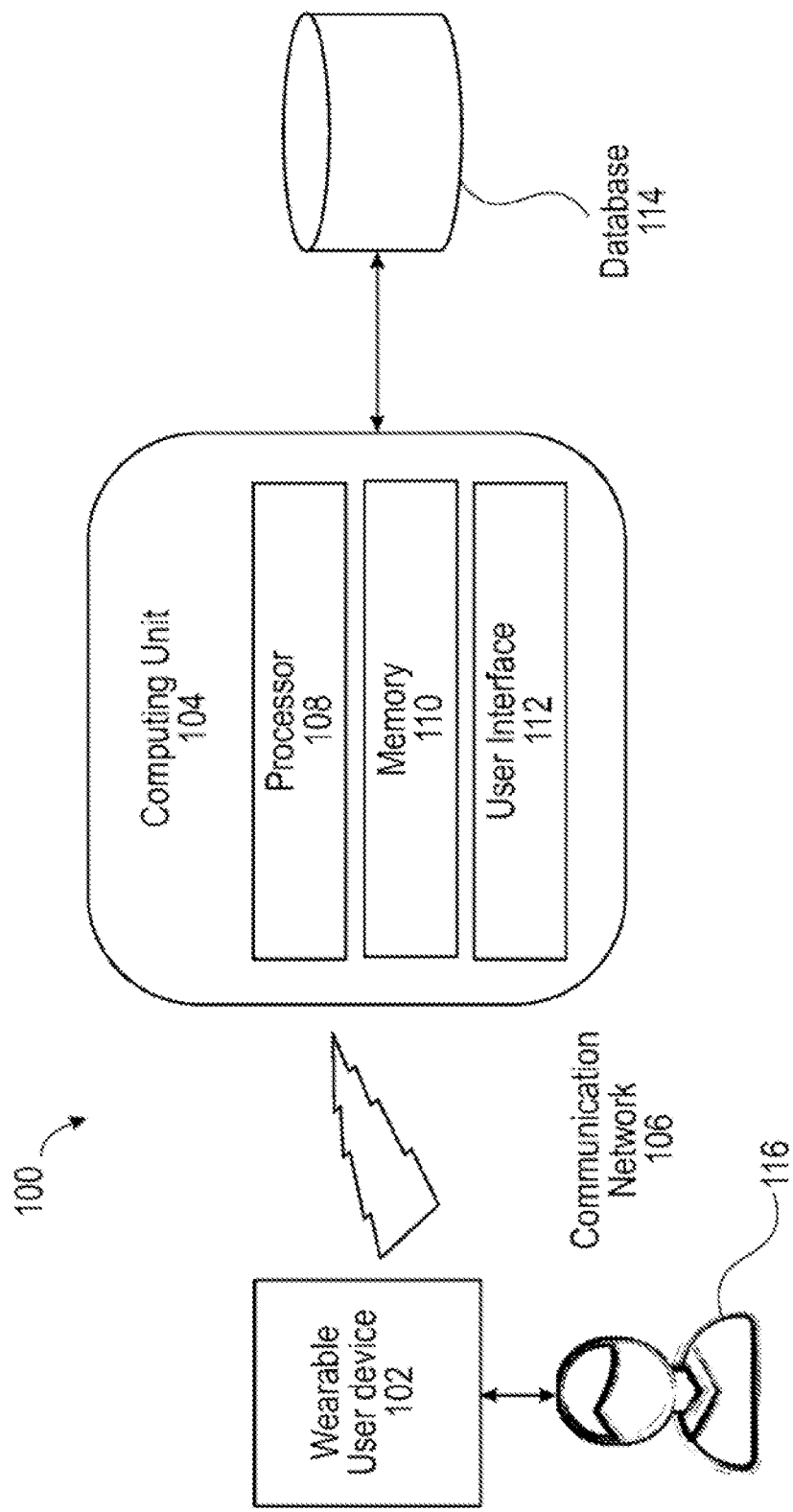
FIG. 1 illustrates a block diagram of the present system to distribute revenue among a plurality of users based on at least one of a quantified emotional data and a qualified emotional data of the corresponding users, in accordance with one embodiment of the present invention.

FIG. 1 illustrates a block diagram of the present system 100 to distribute revenue among a plurality of users based on at least one of a quantified emotional data and a qualified emotional data of the corresponding users, in accordance with one embodiment of the present invention. The system 100 includes a wearable user device 102, and a computing unit 104.

The wearable user device 102 is configured to be worn on the user's 116 body, near the body, or placed in the user's 116 body (implantable) to collect biorhythm data of the user 116. Examples of the wearable user device 102 include but not limited to the implantable, wireless sensor device, smartwatch, smart jewelry, fitness tracker, smart cloth, etc. In an embodiment, the wearable user device 102 includes various sensors to detect one or more parameters pertaining to the emotions of the user 116. In an embodiment, the wearable user device 102 may include a flexible body that can be secured around the user's body to collect the biorhythm data. In an embodiment, and the wearable user device 102 may include a securing mechanism to secure the wearable user device 102 may in a closed loop around a wrist of the user 116. The wearable user device 102 may utilize various wired or wireless communication protocols to establish communication with the computing unit 104.

The computing unit 104 is communicatively connected with the wearable user device 102 to receive the biorhythm data of the users 116 over a communication network 106. Communication network 106 may be a wired or a wireless network, and the examples may include but are not limited to the Internet, Wireless Local Area Network (WLAN), Wi-Fi, Long Term Evolution (LTE), Worldwide Interoperability for Microwave Access (WiMAX), General Packet Radio Service (GPRS), Bluetooth (BT) communication protocols, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), Z-Wave, Thread, 5G, USB, serial, RS232, NFC, RFID, WAN, and/or IEEE 802.11, 802.16, 2G, 3G, 4G cellular communication protocols Examples of the computing unit 104 include but not limited to a laptop, a desktop, a smartphone, a smart device, a smartwatch, a phablet, and a tablet. The computing unit 104 includes a processor 108, a memory 110 communicatively coupled to the processor, and a user interface 112. The computing unit 104 is communicatively coupled with a database 114. The database 114 receives, stores, and processes the emotional data and referral data which can be used for further analysis and prediction so that the present system can learn and improve the analysis by using the historical emotional data and referral data. Although the present subject matter is explained considering that the present system 100 is implemented on a cloud device, it may be understood that the present system 100 may also be implemented in a variety of computing systems, such as an Amazon elastic compute cloud (Amazon EC2), a network server, and the like.

Processor 108 may include at least one data processor for executing program components for executing user- or system-generated requests. A user may include a person, a person using a device such as those included in this invention, or such a device itself. Processor 108 may include specialized processing units such as integrated system (bus) controllers, memory management control units, floating-point units, graphics processing units, digital signal processing units, etc.

Processor 108 may include a microprocessor, such as AMD® ATHLON® microprocessor, DURON® microprocessor OR OPTERON® microprocessor, ARM's application, embedded or secure processors, IBM® POWERPC®, INTEL'S CORE® processor, ITANIUM® processor, XEON® processor, CELERON® processor or other line of processors, etc. Processor 108 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 108 may be disposed of in communication with one or more input/output (I/O) devices via an I/O interface. I/O interface may employ communication protocols/methods such as, without limitation, audio, analog, digital, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Memory 110, which may be a non-volatile memory or a volatile memory. Examples of non-volatile memory may include but are not limited to flash memory, a Read-Only Memory (ROM), a Programmable ROM (PROM), Erasable PROM (EPROM), and Electrically EPROM (EEPROM) memory. Examples of volatile memory may include but are not limited Dynamic Random Access Memory (DRAM), and Static Random-Access memory (SRAM).

The user interface 112 may present the quantified emotional data and qualified emotional data as per the request of an administrator of the present system. In an embodiment, the user interface (UI or GUI) 112 is a convenient interface for accessing the platform and viewing the products or services.

Figure 2:
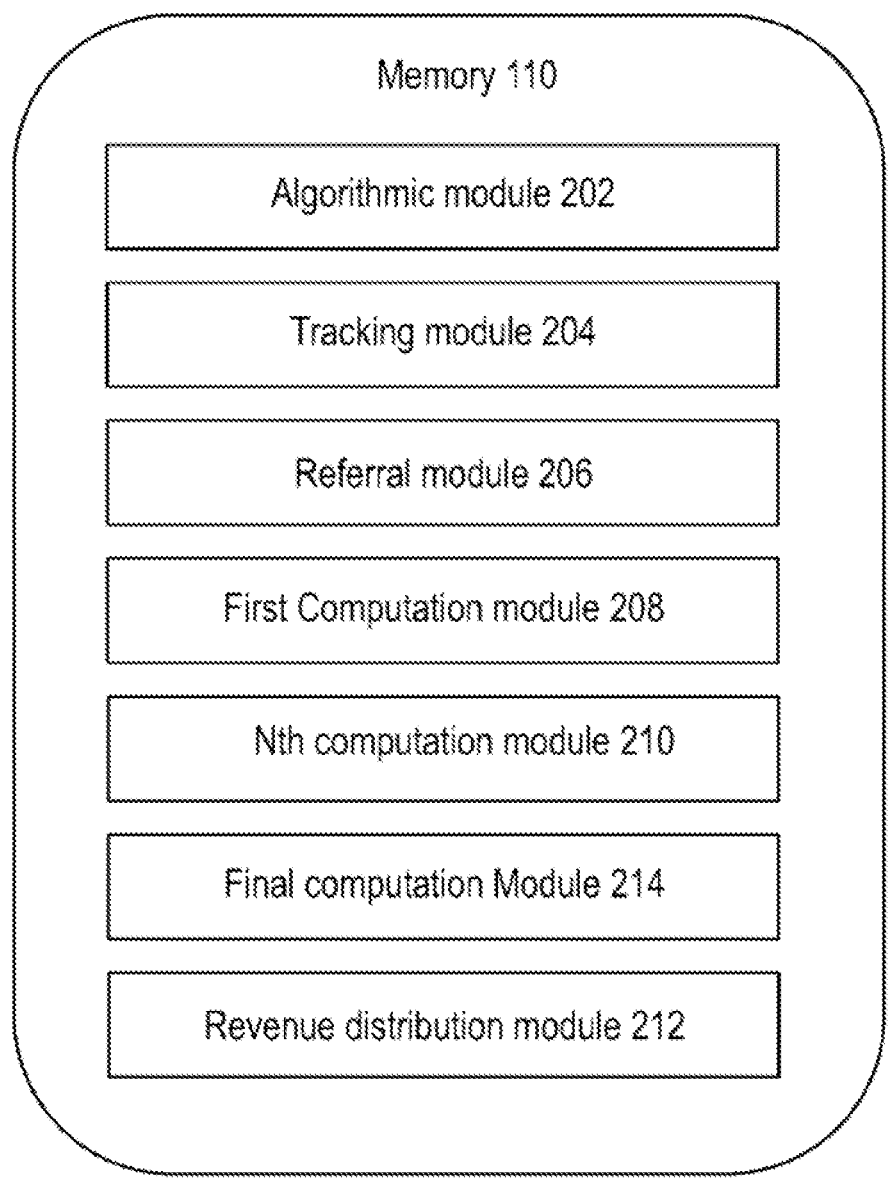
FIG. 2 illustrates a block diagram of the various modules within a memory of a computing unit, in accordance with another embodiment of the present invention.

FIG. 2 illustrates a block diagram of the various modules within a memory 110 of a computing unit 104, in accordance with another embodiment of the present invention. FIG. 2 is explained in conjunction with FIG. 1. The memory 110 includes an algorithmic module 202, a tracking module 204, a referral module 206, a first computation module 208, an nth computation module 210, a final computation module 214, and a revenue distribution module 212. In an embodiment, the memory 110 may independently function as a cloud server to process the functionalities of the modules.

The algorithmic module 202 analyzes the received biorhythm data and compute an emotional score of each user. The tracking module 204 monitors the emotional score of each user. In an embodiment, the algorithmic module 202 is an algorithm which can be executed on various operating systems such as Android, IOS, Windows, and Linux, etc.

The referral module 206 enables the user to send a referral to a plurality of potential users to perform a plurality of actions pertaining to a platform and a product. In an embodiment, the referral module facilitates the users to track the status of the sent referrals and one or more received referrals. In an embodiment, the referral is exclusive for each potential users. In an embodiment, the referral module 206 facilitates the users associated with the referrals to establish communication with each other. In an embodiment, the actions include but not limited to access to the platform and purchase of the product. In an embodiment, the potential users perform the actions by clicking on the referral.

The first computation module 208 computes individual total subscore for each user using the quantified emotional data and the qualified emotional data for an interval of time. Thus individual total scores for each user using the qualitative emotional data, quantitative emotional data and other health data for an interval of time are computed by the first computation module 208. The interval of time could be a week or a month or a year, and these total scores may be calculated periodically e.g. on a monthly basis.

The nth computation module 210 computes at least one subtotal score based on calculations performed on the referrals of each user and a plurality of related referrals corresponding to each user and one or more subtotals based on a plurality of other parameters. The nth computation module 210 computes the subtotal scores for each user based on data of the individual user on the platform. In an embodiment, the nth computation module 210 identifies all the referred users connected to each user and computes a score for each based on set parameters. For example, this may include a plurality of first-generation referrals, a plurality of second-generation referrals, a plurality of third-generation referrals, and a plurality of nth generation referrals. Once the relevant referred users are identified, different calculations may be used to determine a score for each referred user identified. For instance, third-generation referrals may be multiplied by a smaller weight than first-generation referrals. The nth computation module 210 also computes other types of subtotal scores based on the user's data or actions. The final computation module 214 combines the individual subtotal score computed by the first computation module and one or more subtotal scores computed by the nth computation module to obtain a single score for each user. Various orders of operations may be used to perform this calculation.

The revenue distribution module 212 determines a pool of revenue to be allocated for distribution among the users and pulled from one or more company or third party revenue streams. The amount is a portion, percentage, or some calculated amount that is derived from the one or more revenue streams. The revenue distribution module 212 may use various computation methods or equations for different revenue streams. The computation also only takes into consideration revenue from a specific period of time. For example, the computation can be performed over a weekly, biweekly, monthly, or quarterly period. The total revenue for this period would then be split amongst qualifying users based upon further parameters.

Further, the revenue distribution module 212 distributes a predefined amount of money to each user based on a plurality of parameters. This may reward the users who perform better on the platform (have higher individual scores). Higher scores may be achieved by exhibiting/producing healthier physiological data—an outcome of consistent healthier behaviors and habits. Furthermore, the revenue distribution module 212 may set the reward in a way that the users receive the most credit for referring users to the platform. Less credit may be given to new users who sign up through down-chain referrals (second, third or nth level referrals).

Figure 3:
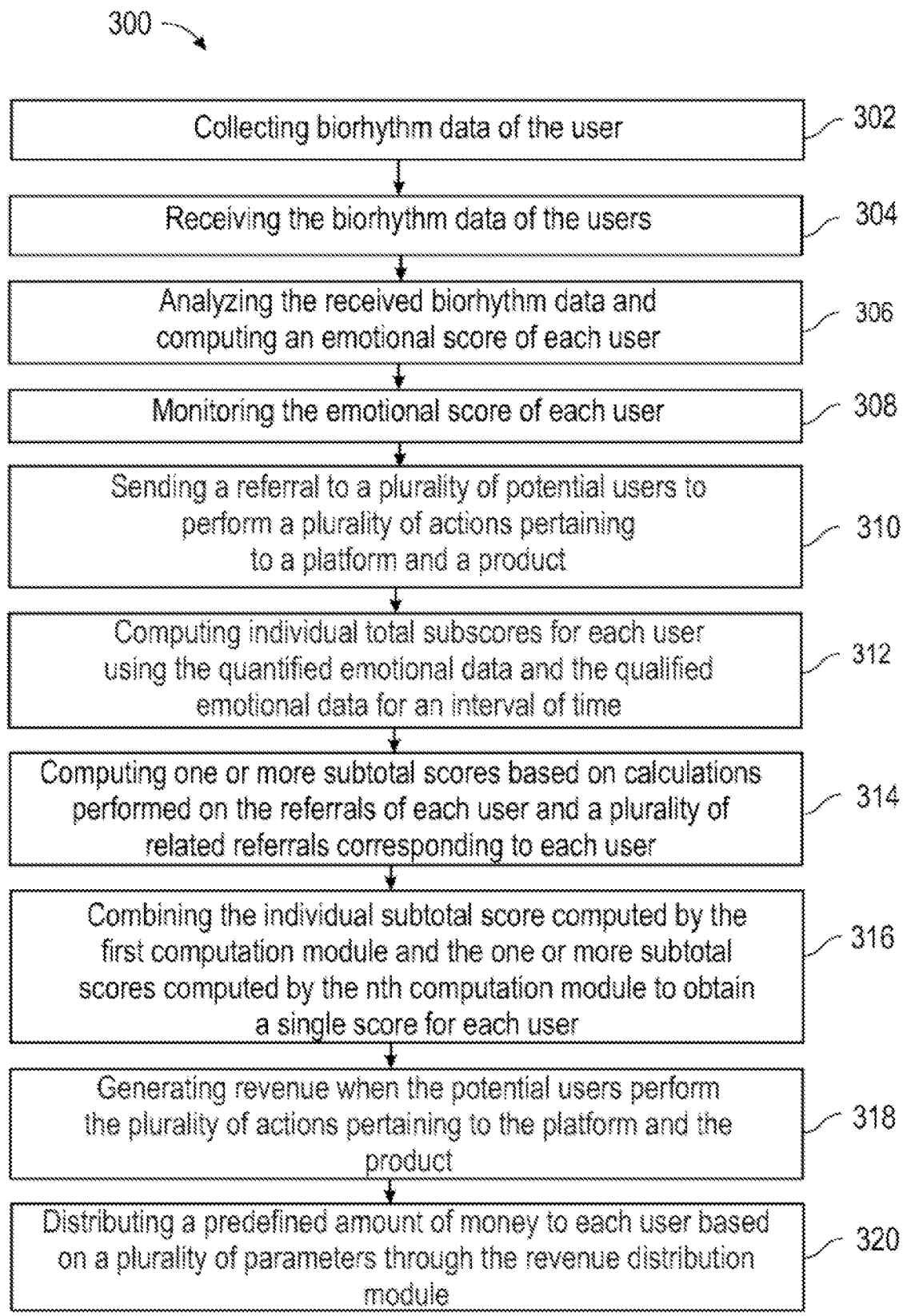
FIG. 3 illustrates a flowchart of the method for distributing revenue among a plurality of users based on at least one of a quantified emotional data and a qualified emotional data of the corresponding users, in accordance with an alternative embodiment of the present invention.

FIG. 3 illustrates a flowchart 300 of the method for distributing revenue among a plurality of users based on at least one of a quantified emotional data and a qualified emotional data of the corresponding users, in accordance with an alternative embodiment of the present invention. The method includes the step 302 of collecting biorhythm data of the user through a wearable user device configured to be worn on the user's body, near the body, or placed in the user's body (implantable). In an embodiment, the wearable user device includes various sensors to detect one or more parameters pertaining to the emotions of the user. In an embodiment, the wearable user device may include a flexible body that can be secured around the user's body to collect biorhythm data.

The method includes the step 304 of receiving the biorhythm data of the users through a computing unit communicatively connected with the wearable user device over a communication network. The method includes the step 306 of analyzing the received biorhythm data and computing an emotional score of each user through an algorithmic module. The method includes the step 308 of monitoring the emotional score of each user through a tracking module.

The method includes step 310 of sending a referral to a plurality of potential users to perform a plurality of actions pertaining to a platform and a product through a referral module. In an embodiment, the referral module facilitates the users to track the status of the sent referrals and one or more received referrals. In an embodiment, the referral is exclusive for each potential users. In an embodiment, the referral module facilitates the users associated with the referrals to establish communication with each other. In an embodiment, the plurality of actions includes access to the platform and purchase of the product. In an embodiment, the potential users perform the actions by clicking on the referral.

The method includes the step 312 of computing individual total sub score for each user using the quantified emotional data and the qualified emotional data for an interval of time through a first computation module. The method includes the step 314 of computing at least one subtotal score based on calculations performed on the referrals of each user and a plurality of related referrals corresponding to each user and one or more subtotals based on a plurality of other parameters through an nth computation module. The nth computation module computes the subtotal scores for each user based on data of the individual user on the platform. In an aspect, the method identifies all the referred users connected to each user and computes a score for each based on set parameters. For example, this may include a plurality of first-generation referrals, a plurality of second-generation referrals, a plurality of third-generation referrals, and a plurality of nth generation referrals. Once the relevant referred users are identified, different calculations may be used to determine a score for each referred user identified. For instance, third-generation referrals may be multiplied by a smaller weight than first-generation referrals. The nth computation module also computes other types of subtotal scores based on the user's data or actions. The method includes the step 316 of combining the individual subtotal score computed by the first computation module and one or more subtotal scores computed by the nth computation module to obtain a single score for each user through a final computation module. Various orders of operations may be used to perform this calculation.

The method includes the step 318 of generating revenue when the potential users perform the plurality of actions pertaining to the platform and the product through a revenue distribution module. The method includes the step 320 of distributing a predefined amount of money to each user based on a plurality of parameters through the revenue distribution module. The parameters comprising at least one of the computed emotional data scores of the users, and a calculation involving of other user's scores present in the user's network on the platform.

Thus the present system and method provide a revenue-sharing and reward-based platform by which the users of the present wearable user device can generate revenue for themselves based on a plurality of predefined parameters. Further, the revenue-sharing and reward-based platform reward the users financially for optimum utilization of the system.

While embodiments of the present invention have been illustrated and described, it will be clear that the invention is not limited to these embodiments only. Numerous modifications, changes, variations, substitutions, and equivalents will be apparent to those skilled in the art, without departing from the scope of the invention, as described in the claims.

The invention claimed is:

1. A method for distributing revenue among users of a computing platform, the method comprising:
   receiving, from a wearable device, biorhythmic data of a user, the biorhythmic data being collected via a sensor integrated into the wearable device;
   deriving emotion data from the biorhythm data;
   determining an emotional sub score of the user from the emotion data, the emotional subscore being higher when the user is exhibiting or producing healthier biorhythm data;
   sending a referral to a plurality of potential users to perform a plurality of actions pertaining to the computing platform;
   computing at least one subtotal score based on calculations performed on the referrals of each user;
   combining the subtotal scores for each user based on data of the individual user on the platform to form a referral subscore;
   receiving the referral subscore of the plurality of referred users, the plurality of referred users being connected to the user;
   determining a revenue score based on the emotional subscore and the referral subscore; and
   attributing a portion of a revenue of the computing platform to the user based on the revenue score.

2. The method of claim 1, wherein the plurality of referred users is organized by a generation of each referral, a weight of the referral subscore being lower for a proximity of the generation of each referral from the user.

3. The method of claim 1, wherein the emotional subscore of the user is calculated over an interval of time.

4. The method of claim 1, wherein the revenue score of the user is adjusted higher.

5. The method of any of claim 1, wherein the biorhythmic data is received in response to a request from an administrator of the computing platform.

* * * * *